United States Patent
Weber et al.

(10) Patent No.: US 6,221,460 B1
(45) Date of Patent: Apr. 24, 2001

(54) LIQUID ABSORBENT MATERIAL FOR PERSONAL CARE ABSORBENT ARTICLES AND THE LIKE

(75) Inventors: Mary Eva Garvie Weber, Alpharetta; Stanley Michael Gryskiewicz, Woodstock, both of GA (US); Pamela Jean Mayberry, Appleton, WI (US); James Arthur Davis, Roswell; Michael Tod Morman, Alpharetta, both of GA (US); Gary Howard Meitner, Winneconne, WI (US); Leslie Warren Collier, IV; Nancy Donaldson Kollin, both of Roswell, GA (US); Douglas Bryan Cole, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/527,284

(22) Filed: Sep. 12, 1995

Related U.S. Application Data (63) Continuation of application No. 08/169,449, filed on Dec. 17, 1993, now abandoned.

(51) Int. Cl.⁷ ........................................ A61F 13/15
(52) U.S. Cl. ..................... 428/131; 428/137; 428/156; 428/168; 428/198; 604/359; 604/368; 604/385.1
(58) Field of Search .................... 428/198, 116, 428/117, 131, 137, 373, 156, 168; 604/359, 368, 385.1

(56) References Cited

U.S. PATENT DOCUMENTS

| | | | |
|---|---|---|---|
| 2,230,903 | 2/1941 | Ostenberg | 128/156 |
| 2,242,937 | 5/1941 | Biederman | 128/285 |
| 2,462,361 | 2/1949 | Cassens | 2/108 |
| 2,544,069 | 3/1951 | Cutler | 128/287 |
| 2,610,496 | 9/1952 | Kostopoulos | 66/176 |

(List continued on next page.)

FOREIGN PATENT DOCUMENTS

| | | | |
|---|---|---|---|
| 647987 | 7/1993 | (AU) . | |
| 0 067 916 | 12/1982 | (EP) . | |
| 0067916 | 12/1982 | (EP) . | (EP) . |

(List continued on next page.)

OTHER PUBLICATIONS

Examiner's report to the Comptroller under Section 17, Application No. GB9425480.2.

*Primary Examiner*—Elizabeth M. Cole
(74) *Attorney, Agent, or Firm*—Patrick C. Wilson (57) ABSTRACT

Disclosed herein is a liquid absorbent material that is particularly useful as a liner material for personal care absorbent articles such as diapers, training pants, incontinence garments, sanitary napkins, bandages and the like. The material contains a plurality of peaks across its surface at spaced-apart intervals separated by channels. Disposed within the peaks is a liquid absorbing material capable of absorbing body exudates and liquids in general. Due to the materials and the nature of the construction of the present invention, when used as a liner material for personal care absorbent articles such as diapers, it tends to reduce the total surface area in contact with the infant's skin and it also provides a plurality of air channels within the diaper from the front waistband to the back waistband of the diaper thereby providing a path for increased air circulation. The material of the present invention has other uses as, for example, a packing or liner material for packaging and shipping materials containing liquids. In addition, the peaks can contain other additive such as soaps so the material can be used as a wash pad or cloth.

60 Claims, 5 Drawing Sheets

U.S. PATENT DOCUMENTS

| | | | |
|---|---|---|---|
| 2,880,727 | 4/1959 | Whalen | 128/288 |
| 3,073,309 | 1/1963 | Mosier | 128/290 |
| 3,081,772 | 3/1963 | Brooks et al. | 128/287 |
| 3,121,427 | 2/1964 | Mosier | 128/284 |
| 3,122,754 | 3/1964 | Wedin | 2/113 |
| 3,150,665 | 9/1964 | May, Jr. et al. | 128/288 |
| 3,315,676 | 4/1967 | Cooper | 128/287 |
| 3,340,875 | 9/1967 | Dudley et al. | 128/290 |
| 3,381,638 | 5/1968 | Satas | 128/296 |
| 3,423,266 | 1/1969 | Davies et al. | 156/167 |
| 3,692,618 | 9/1972 | Dorschner et al. | 161/72 |
| 3,802,817 | 4/1974 | Matsuki et al. | 425/66 |
| 3,863,637 | 2/1975 | MacDonald et al. | 128/287 |
| 3,932,322 | 1/1976 | Duchane | 260/17.4 |
| 4,029,101 | 6/1977 | Chesky et al. | 128/290 |
| 4,032,681 | 6/1977 | Jonnes | 428/253 |
| 4,041,951 | 8/1977 | Sanford | 128/287 |
| 4,059,114 | 11/1977 | Richards | 128/287 |
| 4,079,152 | 3/1978 | Bedrosian et al. | 426/124 |
| 4,091,137 | 5/1978 | Miller | 428/198 |
| 4,195,634 | 4/1980 | Bengtsson et al. | 2/81 |
| 4,236,257 | 12/1980 | Williams et al. | 2/406 |
| 4,340,563 | 7/1982 | Appel et al. | 264/518 |
| 4,341,213 | 7/1982 | Cohen | 128/284 |
| 4,423,080 | 12/1983 | Bedrosian et al. | 426/124 |
| 4,451,934 | 6/1984 | Gioello | 2/113 |
| 4,568,341 | 2/1986 | Mitchell et al. | 604/368 |
| 4,578,070 | 3/1986 | Holtman | 604/378 |
| 4,655,760 | 4/1987 | Morman et al. | 604/385 |
| 4,681,577 | 7/1987 | Stern et al. | 604/378 |
| 4,681,793 | 7/1987 | Linman et al. | 428/138 |
| 4,685,914 | 8/1987 | Holtman | 604/368 |
| 4,704,116 | 11/1987 | Enloe . | |
| 4,710,189 | 12/1987 | Lash | 604/385 |
| 4,756,725 | 7/1988 | Peace | 55/275 |
| 4,758,240 | 7/1988 | Glassman | 604/379 |
| 4,761,322 | 8/1988 | Raley | 428/198 |
| 4,826,497 | 5/1989 | Marcus et al. | 604/359 |
| 4,840,734 | 6/1989 | Johnson | 210/660 |
| 4,883,549 | 11/1989 | Frost et al. | 156/161 |
| 4,887,602 | 12/1989 | O'Leary | 604/305.1 |
| 4,895,568 | 1/1990 | Enloe | 604/385.2 |
| 4,900,317 | 2/1990 | Buell | 604/370 |
| 4,904,251 | 2/1990 | Igaue et al. . | |
| 4,961,982 | 10/1990 | Taylor | 428/41 |
| 4,977,011 | 12/1990 | Smith | 428/152 |
| 4,981,747 | 1/1991 | Morman | 428/198 |
| 4,990,541 | 2/1991 | Nielsen et al. | 521/70 |
| 5,004,465 | 4/1991 | Ternstrom et al. | 604/385.1 |
| 5,019,062 | 5/1991 | Ryan et al. | 604/359 |
| 5,066,527 | 11/1991 | Newell | 428/35.6 |
| 5,114,781 | 5/1992 | Morman | 428/198 |
| 5,128,193 | 7/1992 | Anapol et al. | 428/171 |
| 5,137,525 | 8/1992 | Glassman | 604/385.1 |
| 5,151,091 | 9/1992 | Glaug et al. | 604/385.1 |
| 5,167,654 | 12/1992 | Yang | 604/385.2 |
| 5,171,236 | 12/1992 | Dreier et al. | 604/369 |
| 5,197,959 | 3/1993 | Buell | 604/385.1 |
| 5,211,641 | 5/1993 | Roos et al. | 604/385.1 |
| 5,382,246 | 1/1995 | Kawano | 604/385.2 |
| 5,383,870 | 1/1995 | Takai et al. | 604/378 |
| 5,387,209 | 2/1995 | Yamamoto et al. | 604/384 |
| 5,418,045 | 5/1995 | Pike et al. | 428/198 |
| 5,427,838 | 6/1995 | Yamamoto et al. | 428/167 |

FOREIGN PATENT DOCUMENTS

| | | | |
|---|---|---|---|
| 219969 B1 | 9/1986 | (EP) . | |
| 0321985 | 6/1989 | (EP) . | |
| 422504 | 4/1990 | | |
| 0518340 | 12/1992 | (EP) . | |
| 0 565 718 | 10/1993 | (EP) . | |
| 0 631 860 | 1/1995 | (EP) . | |
| 2 350 830 | 5/1977 | (FR) . | |
| 2 653 328 | 4/1991 | (FR) . | |
| 2058455 | 4/1981 | (GB) . | |
| 2 097 722 | 8/1985 | (GB) . | |
| 2259018 | 8/1991 | (GB) . | |
| 2275611 | 9/1994 | (GB) . | |
| 6-315501 | 11/1993 | (JP) . | |
| 7-119012 | 5/1995 | (JP) | D04H/1/54 |
| 260954 | of 1995 | (TW) . | |
| 89/01325 | 2/1989 | (WO) . | |
| 91/19033 | 5/1991 | (WO) . | |
| WO9109582 | 7/1991 | (WO) . | |
| WO9111161 | 8/1991 | (WO) . | |
| 93/01342 | 1/1993 | (WO) . | |
| WO 94/05243 | 3/1994 | (WO) . | |
| WO 94/05244 | 3/1994 | (WO) . | |

LIQUID ABSORBENT MATERIAL FOR PERSONAL CARE ABSORBENT ARTICLES AND THE LIKE

This application is a continuation of application Ser. No. 08/169,449 entitled "LIQUID ABSORBENT MATERIAL FOR PERSONAL CARE ABSORBENT ARTICLES AND THE LIKE" and filed in the U.S. Pat. No. and Trademark Office on Dec. 17, 1993, now abandonded.

BACKGROUND OF THE INVENTION

The present invention is directed to a liquid absorbing liner material. More particularly, the present invention is directed to a liquid absorbing liner material that is suitable as a body-side liner material for personal care absorbent articles including diapers, feminine pads, incontinence garments and training pants.

Diaper dermatitis is a skin condition that results from the prolonged contact of wet occlusive diapers with the skin of the wearer. This prolonged contact can lead to excessive hydration of the stratum corneum or outermost skin layer, thus reducing the skin's ability to function as a barrier. When the barrier properties of the skin are compromised, there is an increase in the permeation of irritants, the susceptibility of the skin to physical damage and the invasion of the skin by microorganisms. Maintaining a normal skin hydration level helps the skin maintain its optimum barrier properties. For this reason, it is important that personal care absorbent products, to the extent possible, prevent excessive skin hydration while containing body exudates and providing a soft, dry and comfortable feel to the wearer.

Current occlusive absorbent garments with flat liners hold body exudates, specifically urine and feces, against the skin of the wearer. Heat and moisture are prevented from escaping from the product due to the close fitting nature of the product designed to prevent leakage. This problem is most severe in the insult region of personal care absorbent products. The flat liner provides a high contact area with the skin which can act as a pathway to conduct back to the skin free liquid that is not locked up by the absorbent core, especially when the product is under pressure at the insult point since the flat liner cannot provide a sufficient degree of separation of the wearer from the free liquid. In addition, the flat liner does not allow the insult region of the personal care absorbent product to communicate with the ambient air to allow humidity to be reduced in the insult region as well as away from the insult region.

Methods have been described to achieve communication of the interior region of a personal care absorbent product with the ambient air including breathable backsheets, waist vents and leg vents. These methods have various deficiencies that make them less effective than desired to achieve normal, unoccluded skin hydration levels. Breathable backsheets provide a pathway for drying through the backsheet to the interior of the absorbent product. However, the wet absorbent can hinder the true communication of the skin with the ambient air. Waist and leg vents through the backsheet tend to either be occluded against the skin or provide leakage pathways. Other methods discuss the use of folded absorbent cores or layers under the liner to dry the liner (skin contact) layer. These methods call for undesirable process options and economics and do not truly allow the ambient air to dry the skin of the wearer—rather, they dry the skin contact layer. As a result, there is a need for a material that can be used for, among other things, a liner material for personal care absorbent products such as diapers, training pants, incontinence garments, sanitary napkins, bandages and the like to reduce the humidity in the insult area and the skin hydration level of the wearer.

SUMMARY OF THE INVENTION

It is an object of the present invention to provide a liner for a disposable absorbent garment that improves upon the above disadvantages of current disposable absorbent garments. Thus, it is desired to provide a liner composite that will allow the insult region and areas away from the insult region to communicate through air passageways or channels with the ambient air to provide reduced humidity in all regions in the personal care absorbent product and, at the same time, provide suitable absorbent properties to provide low leakage in a personal care absorbent product even when subjected to the pressure of the wearer. In addition, the liner composite should have a soft, dry feel and contain minimal free liquid at the skin contact regions after insult to reduce wearer discomfort and skin hydration.

To allow the ambient air to reach the skin of the wearer, the composite structure of the present invention is provided with resilient, crush-resistant raised skin contact areas or peaks and air passageways or channels formed between the raised skin contact areas to provide desired functional characteristics including humidity reduction thereby promoting the desired maintenance of normal skin hydration along with the desired absorbency and comfort properties. The structure, geometry and the selection of the construction materials that form the overall material are important aspects of the invention as will be described in further detail below.

It is a another object of the present invention to provide a means for separating feces from the skin of the wearer to reduce irritation of the skin. Separation of the feces from the skin of the wearer is possible with the present invention due to the ability of the liner material to store the feces in the areas between the raised areas of the liner.

The liquid absorbing liner material of the present invention can be configured in a number of ways. In a first embodiment, the liquid absorbing liner material includes a facing layer and a support layer with the facing layer being joined to the support layer by a plurality of spaced-apart bonds such that between the pairs of bonds the facing layer and support layer form a plurality of peaks which can be filled with various types of liquid absorbing material. Disposed between the peaks are a plurality of channels which separate the peaks from one another and permit air flow along the length of the material.

In a second embodiment the liquid absorbing liner material does not use a support layer. Instead, the facing layer contains a plurality of first and second folds which each form respective first and second fold lines. The facing layer is joined to itself generally along these first and second folds to again form a plurality of spaced-apart peaks which can be filled with various types of liquid absorbing material. As with the previous embodiment, the peaks are separated by a plurality of channels which again serve to permit air flow between the peaks.

In yet a third embodiment of the present invention, the liquid absorbing liner material comprises a facing layer with a plurality of individually formed peaks which are attached to the surface of the facing layer at spaced-apart intervals. In this embodiment, the peaks are preformed and can be unwound from supply rolls and then attached directly to the facing layer.

The liquid absorbing liner material of the present invention has a variety of uses not the least of which is as a liner material for personal care absorbent articles. Such articles typically include a liner material and a backsheet with an absorbent core disposed therebetween. The liquid absorbing liner material of the present invention can be used as the liner material in the personal care absorbent article. Due to the liquid absorbing capacity of the peaks of the liquid absorbing liner material of the present invention, it is also possible to create personal care absorbent articles wherein the article comprises a liner material and a backsheet joined to the liner material with the area between the liner and backsheet being devoid of any type of absorbent core due to the functional properties of the peaks of the liquid absorbing liner material.

A further understanding of the present invention can be gained by a review of the following specification, claims and drawings.

DETAILED DESCRIPTION OF THE INVENTION

Figure 1:
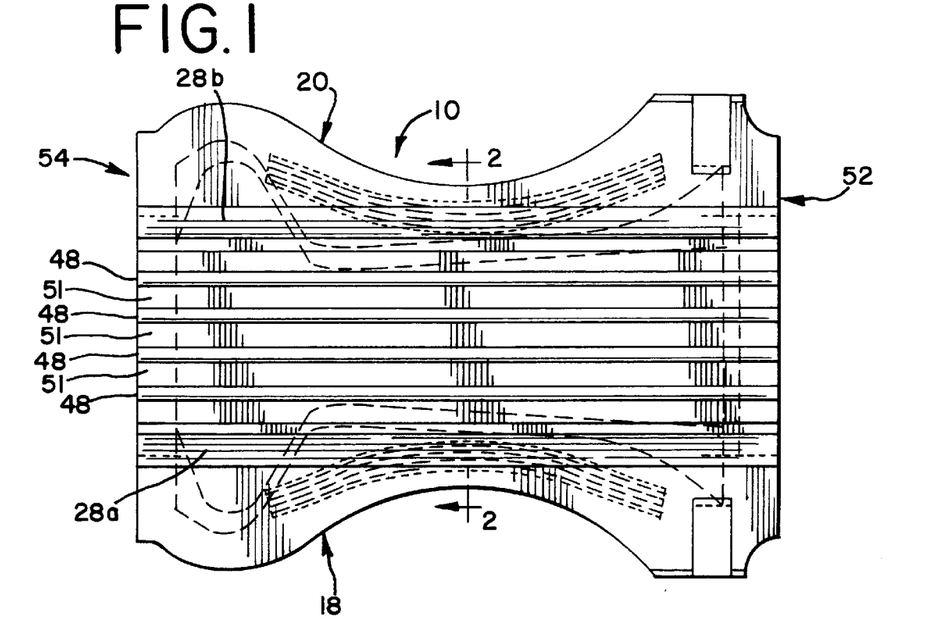
FIG. 1 is a top plan view of a personal care absorbent article, in this case a diaper, utilizing a liquid absorbing liner material according to the present invention.
Figure 2:
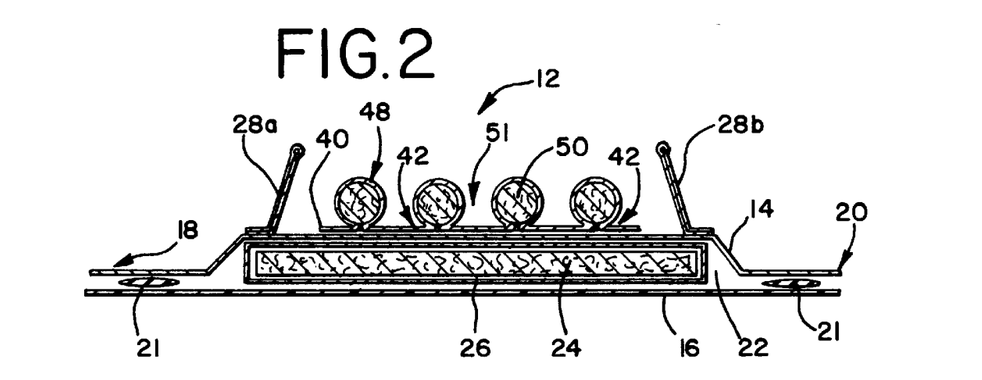
FIG. 2 is a cross-sectional side view along line 2—2 of the diaper shown in FIG. 1.
Figure 3:
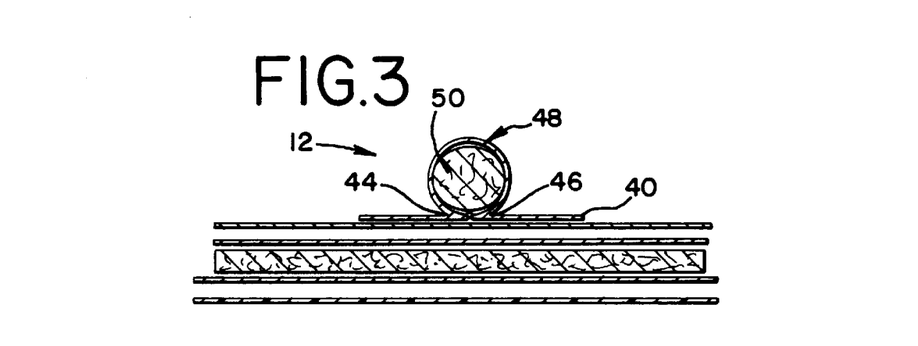
FIG. 3 is an enlarged view of one of the liquid absorbing peaks according to the present invention from FIG. 2.

Referring to FIGS. 1 through 3 there is shown a personal care absorbent article 10, in this case a diaper. The diaper 10 has a liquid absorbing liner 12, a separation sheet 14 and a backsheet 16. The separation sheet 14 and the backsheet 16 can be joined to one another along a left side edge 18 and a right side edge 20 by an adhesive 21 or other means 21 thereby defining a cavity 22 therebetween. Disposed within the cavity 22 is an absorbent core 24 such as wood pulp fluff which may or may not be wrapped with a tissue wrap 26. Interior to the left side edge 18 and right side edge 20 are leg dams 28a and 28b which serve to help retain body fluids such as urine, feces and menses within the personal care absorbent article. The leg dams 28a and 28b extend upwardly from the same side of the separation layer 14 as the liner material 12 and define zones between the leg dams and the left and right sides respectively which are essentially devoid of the liner material 12. The liner 12 may be attached to the separation sheet 14 by such means as adhesives, needling, stitching, thermomechanical bonding and ultrasonic bonding collectively referred to as "bonding".

While the foregoing is a general description of a diaper design, this design can be modified and still utilize the liquid absorbing liner material 12 of the present invention. For example, the separation layer 14 can be removed and the liner 12 can be extended all the way across the diaper 10 from left side edge 18 to the right side edge 20 and then joined to the backsheet 16 to define the cavity 22. In addition, the liner 12 of the present invention can be used as the liner material for all types of personal care absorbent articles including, but not limited to, feminine pads or sanitary napkins, training pants, incontinence garments, bandages and the like. Furthermore, the liquid absorbing liner material of the present invention can be used as a packaging or liner material for shipping and storing goods, especially those containing liquids. This is because the peaks in the liner 12 act as padding but also have the capability of absorbing liquids. As a result, if there is a liquid spill within the package, leakage to other packages will be reduced. The peaks also can be filled with such things as soaps and medicaments which can be later dispensed through emersion in solvents or by pressure. Consequently, any use wherein a liquid absorbing material is needed is also contemplated to be within the scope of the present invention.

Turning in more detail to the liquid absorbing liner material 12 and in particular to the cross-section of FIGS. 2 and 3, the liner 12 includes a facing layer 40 containing a plurality of pleats 42 formed by creating a plurality of pairs of inwardly facing first and second folds 44 and 46 which are joined or bonded to one another continuously or intermittently along the length of the liner 12 to form a plurality of peaks 48 separated by channels 51. The inwardly facing first and second folds 44 and 46 may be joined to one another in either a butting or overlapping relationship using one or more of the aforementioned appropriate means of bonding. The use of an adhesive has been found to be most advantageous and the adhesive may be applied intermittently or along the entire length of the folds. Suitable adhesives include, but are not limited to, water-based adhesives, solvent-based adhesives and hot melt adhesives.

The purpose of the facing layer 40 is to allow passage of various liquids and body exudates such as feces, urine and menses, collectively referred to herein as "liquids" and also used interchangeably with the term "body exudates," through to the liquid absorbent material 50. As a result, the facing layer 40 should be liquid permeable and pass liquids through while retaining none or only a minimal amount of the liquid. Consequently, the facing layer can be made from a wide variety of materials including, but not limited to, woven materials such as cloth, knit materials, permeable films, foams and fibrous nonwoven materials. Combinations of the foregoing as in multi-layer configurations or laminates can also be used to impart specifically tailored properties. The facing layer 40 can contain perforations, holes, openings or voids that are aligned either along the peaks 48 and/or the channels 51 or randomly in the facing layer 40.

These openings can facilitate fluid transfer through the facing layer into either the liquid absorbent material 50 or through the separation sheet 14 into the absorbent core 24 disposed below the liner 12 and separation sheet 14. Due to the low cost, good liquid handling properties and excellent variability, the examples set forth below used fibrous nonwoven webs for the facing layer 40.

Fibrous nonwoven webs can be made from both synthetic and natural fibers as well as combinations of the two. Examples of natural fibers include, but are not limited to, cotton, rayon, wool and wood. The fibers may be single strand fibers or yarns. Examples of synthetic fibers include, but are not limited to, thermoplastic fibers made from polyolefins, polyesters and polyamides. The fibers may be short, staple length fibers such as are used in carded webs or longer, more continuous fibers as are used in meltblown and spunbonding processes. The fibers, themselves, may be straight or crimped, solid or hollow, single constituent such as polypropylene fibers or a multi-constituent fibers such as a bicomponent fibers. When using bicomponent or multi-component fibers they can include sheath/core, side-by-side and islands in the sea fiber designs. Circular as well as irregular cross-sections fibers are also usable with the present invention.

The fibers may be formed into nonwoven webs using a variety of processes including, air laying, wet laying, solution spinning, carding and bonding, meltblowing and spunbonding. Basis weights for the webs may vary depending on the particular end use. When used as a liner for personal care applications, basis weights for the facing layer 40 will typically range between about 0.3 and about 2.5 ounces per square yard (osy) (about 10 to about 85 grams per square meter).

The fibers and/or the resultant fibrous nonwoven webs used to make the facing layer 40 may incorporate or be treated with a chemical to achieve a surface energy that allows liquid to pass through without being retained on the fiber surface, inside the fiber or in the interstitial spaces between the fibers. Surfactants may be added internally to the polymer extrusion mix and then bloomed to the surface of the fibers or they may be topically added as by the use of a solution spray.

Disposed within the peaks 48 formed by the facing layer 40 is a liquid absorbent material 50, the purpose of which is to absorb liquids entering through the facing layer 40. Depending on the nature of the liquid absorbent material 50, the material can be designed to hold the liquid and/or transfer all or a portion of the liquid to the absorbent core 24 within the cavity 22 or to adjacent peaks 48. Suitable materials for the liquid absorbent material 50 include, but are not limited to, cotton fluff, tissue, woven materials, tow and especially nonwoven materials as well as combinations of the foregoing. Blends of both natural and synthetic fibers also work well.

It is desirable that the material chosen be fairly resilient, resistant to deformation and not collapse, especially when wet, so that the peaks 48 will not unduly collapse when they are soaked with liquid and placed under pressure such as when a baby sits down while wearing a diaper. To this end, nonwoven materials that are made from fibers that are bondable to one another are especially advantageous. Thermoplastic fibers made from such polymers as polyolefins, polyesters and polyamides work well as do multiconstituent fibers such as bicomponent fibers with sheath/core, side-by-side and island in the sea fiber designs. Bicomponent fibers are typically bonded to one another by techniques including through air bonding. Other fiber/nonwoven web bonding techniques include thermomechanical bonding, ultrasonic bonding and powder bonding. Basis weights for the liquid absorbent material 50 when used in personal care articles will usually range between about 0.3 and about 7.0 ounces per square yard. (about 10 to about 240 grams per square meter).

A particularly well-suited spunbonded nonwoven web for the liquid absorbent material 50 is made from side-by-side polyethylene/polypropylene spunbond bicomponent fibers. The process for forming such fibers and resultant webs includes using a pair of extruders for separately supplying both the polyethylene and the polypropylene to a bicomponent spinneret. Spinnerets for producing bicomponent fibers are well known in the art and thus are not described herein. In general, the spinneret includes a housing containing a spin pack which includes a plurality of plates having a pattern of openings arranged to create flow paths for directing the high melting and low melting polymers to each fiber-forming opening in the spinneret. The spinneret has openings arranged in one or more rows and the openings form a downwardly extending curtain of fibers when the polymers are extruded through the spinneret. As the curtain of fibers exit the spinneret, they are contacted by a quenching gas which at least partially quenches the fibers and develops a latent helical crimp in the extending fibers. Oftentimes the quenching air will be directed substantially perpendicular to the length of the fibers at a velocity of from about 100 to about 400 feet per minute at a temperature between about 45 and about 90° F.

A fiber draw unit or aspirator is positioned below the quenching gas to receive the quenched fibers. Fiber draw units or aspirators for use in meltspinning polymers are well known in the art. Exemplary fiber draw units suitable for use in the process include linear fiber aspirators of the type shown in U.S. Pat. No. Number 3,802,817 to Matsuki et al. and eductive guns of the type shown in the U.S. Pat. No. 3,692,618 to Dorshner et al., U.S. Pat. No. 3,423,266 to Davies et al and U.S. Pat. No. 4,340,563 to Appel et al. The fiber draw unit in general has an elongated passage through which the fibers are drawn by aspirating gas. The aspirating gas may be any gas, such as air that does not adversely interact with the polymers of the fibers. The aspirating gas can be heated as the aspirating gas draws the quenched fibers and heats the fibers to a temperature that is required to activate the latent crimps therein. The temperature required to activate the latent crimping within the fibers will range from about 110° F. to a maximum of less than the melting point of the low melting component polymer which, in this case, is the polyethylene. Generally, a higher air temperature produces a higher number of crimps.

The drawn and crimped fibers are deposited onto a continuous forming surface in a random manner, generally assisted by a vacuum device placed underneath the forming surface. The purpose of the vacuum is to eliminate the undesirable scattering of the fibers and to guide the fibers onto the forming surface to form a uniform unbonded web of bicomponent fibers. If desired, the resultant web can be lightly compressed by a compression roller before the web is subjected to a bonding process.

To bond the bicomponent spunbonded web a through-air bonder is used. Such through-air bonders are well known in the art and therefore need not be described in detail. In the through-air bonder, a flow of heated air is applied through the web to heat the web to a temperature above the melting point of the lower melting point component of the bicomponent fibers but below the melting point of the higher melting point component. Upon heating, the lower melting polymer portion of the web fibers are melted and the melted portions of the fibers adhere to adjacent fibers at the crossover points while the high melting polymer portions of the fibers tend to maintain the physical and dimensional integrity of the web.

The liquid absorbent material 50 may be formed in the general shape of the peaks 48 or it may be formed in sheet form and then rolled, folded or stacked to fit into the peaks 48. Examples of folding patterns include fan or "W" folds, "C" folds, "U" folds and scroll or spiral folds. See FIGS. 6a through 6e. Other folding patterns are also considered to be within the scope of the present invention.

As mentioned previously, the liquid absorbent material 50 within the peaks 48 may be designed to perform multiple fluid handling functions. As a result, it is possible to place other components within the peaks 48 or directly within the liquid absorbent material 50. Examples of such other components include, but are not limited to, wood pulp, fluff, tissue, superabsorbent particles and fibers, odor reducing agents and antimicrobial agents. Superabsorbent materials, whether in particulate, fiber or other form, should be able to absorb at least four times their own weight in water.

As shown in the Figures, the peaks 48 can be long continuous tubes of generally equal diameter and spacing separated by channels 51 that extend to the ends of the absorbent article. This too can be varied. For example, the number of peaks can be varied and the spacing between the peaks can be increased or decreased. Also, the spacing between the various peaks 48 can be unequal as, for example, closer in the central region of the diaper to give the diaper liner 12 greater crush resistance and farther apart at the edges of the diaper to give more air flow through the diaper via the channels 51 from the top back edge 52 of the diaper to the top front edge 54 for ventilation. The peaks 48 can have different cross-sectional shapes including for example, round, oval, square, rectangular and trapezoidal. The length of the peaks 48 can also be varied and they can be noncontinuous, staggered, broken or segmented however, they should extend beyond the ends of the absorbent core and more desirably to the ends of the product. The ends of the peaks 48 can be finished off at the top back edge 52 and top front edge 54 of the diaper by means such as by tapering them down to a point or pinching them off. If particulate superabsorbents are being used in the peaks 48 then this is particularly important so as to avoid shake-out of the particles. In addition, the direction of the channels can be varied though for maximum air flow through the diaper it is best to keep the peaks 48 running along the length of the diaper 10. Combinations of the foregoing variables are also possible.

Due to the use of nonwovens, it is possible to create materials with varying pore sizes and pore size gradients. To create capillary action within and through the plurality of pores in a fibrous nonwoven web it is best to form a pore size gradient from the first exterior surface of the web to the second exterior surface with the pores adjacent the first exterior surface being larger than the pores adjacent the second exterior surface. Liquid entering the larger pores will be drawn down and through the web structure to the smaller pores. Consequently, by folding such a material over on itself such that the second exterior surface with the smaller pores contacts itself, the first exterior surface with the larger pores will be exposed. Folding the liquid absorbent material in this manner and placing it inside the peaks will allow liquid entering the peaks to be drawn inwardly and retained.

Referring to FIGS. 1 and 2 of the drawings, the diaper 10 has a total width in the crotch of approximately eight inches (20 centimeters) and the width between the leg dams 28a and 28b is approximately four inches (10 centimeters). In the area between the leg dams, the liner material 12 includes four peaks each of which has a height or diameter which is generally equal to the spacing between the peaks. In this particular case the diameter of the peaks 48 is approximately one-half inch (12.7 mm) and the spacing between the peaks 48 is approximately one-half inch (12.7 mm).

A stated objective of the present invention is to provide a liner material which takes liquids away from the wearer's skin and provides air circulation to promote skin wellness. If the height of the peaks is too low or the spacing too wide, then the stated objectives will be compromised. Similarly, if the spacing is too tight, air flow within the channels 51 may not be as great. Consequently, when designing the particular liner material, factors such as loading, wet and dry compression resilience, pressure and overall capacity should be taken into account.

The liner material 12 once designed can be attached to one or more of the other components of the diaper or other personal care absorbent article using any number of conventional means including adhesives, needling, stitching, thermomechanical or ultrasonic bonding again collectively referred to as "bonding". Care should be taken, however, to adjust the degree of bonding to provide sufficient structural rigidity while still maintaining fluid transport capabilities.

Figure 4:
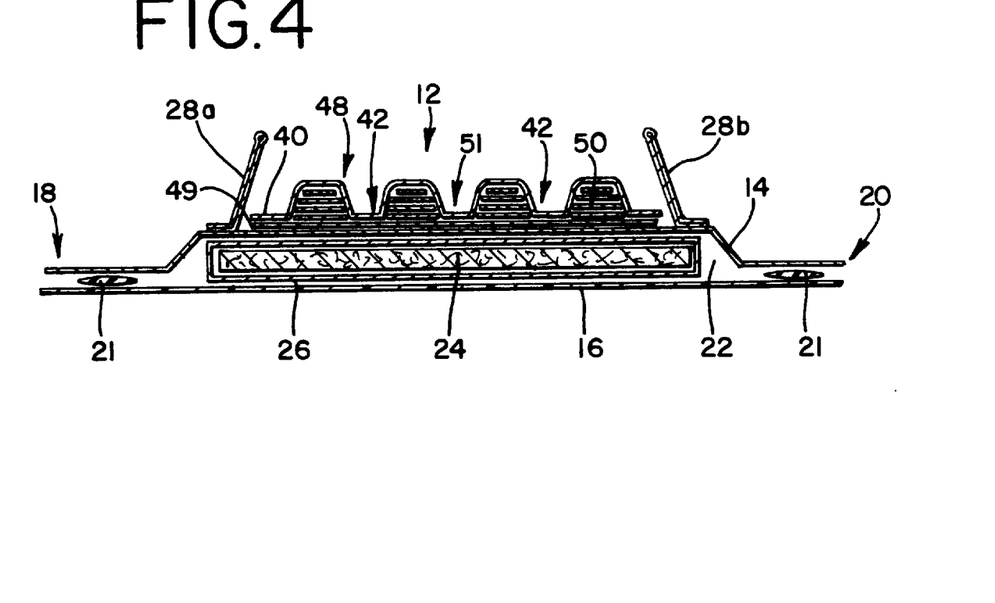
FIG. 4 is a cross-sectional side view of a diaper like that shown in FIG. 1 with an alternate embodiment of a liquid absorbing liner material according to the present invention.
Figure 5:
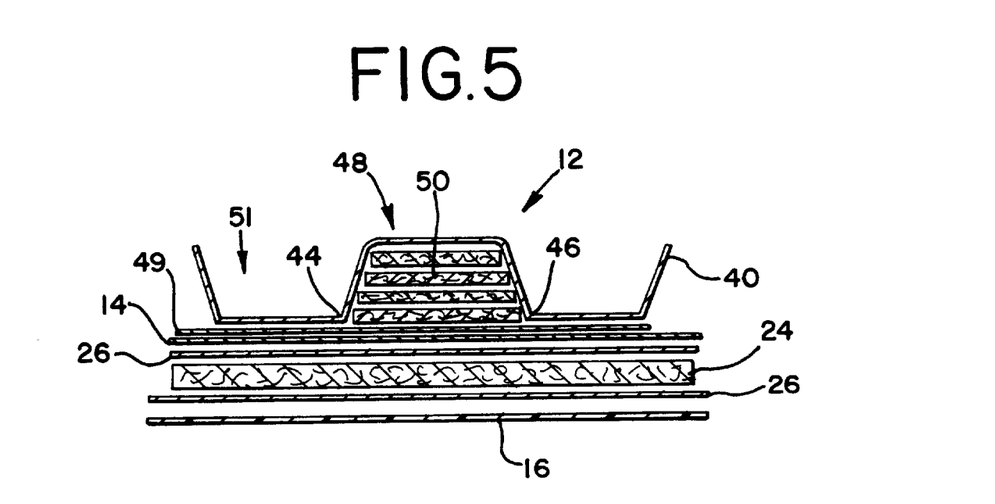
FIG. 5 is an enlarged view of one of the liquid absorbing peaks according to the present invention from FIG. 4.
Figure 6A:
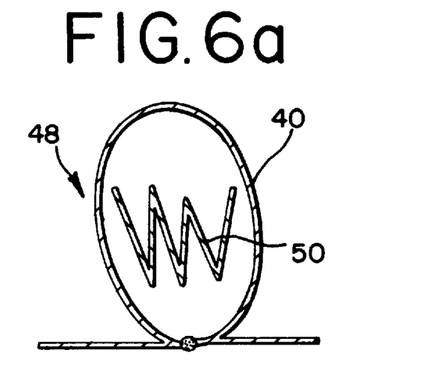
FIGS. 6a, 6b, 6c, 6d and 6e are cross-sectional side views of several ways the liquid absorbent material within the peaks according to the present invention can be folded when sheet-based material is being used to fill the peaks.
Figure 6B:
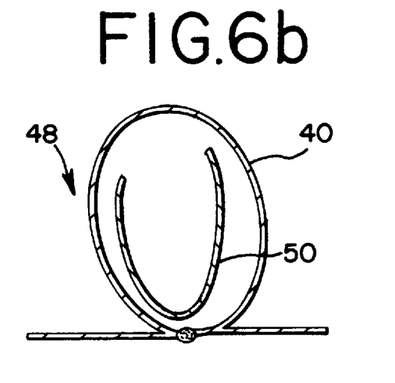
Figure 6C:
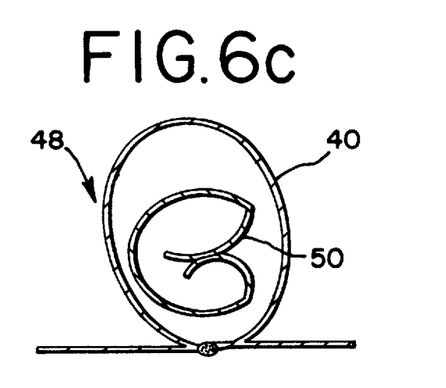
Figure 6D:
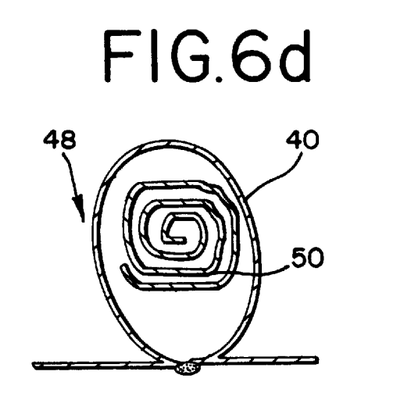
Figure 6E:
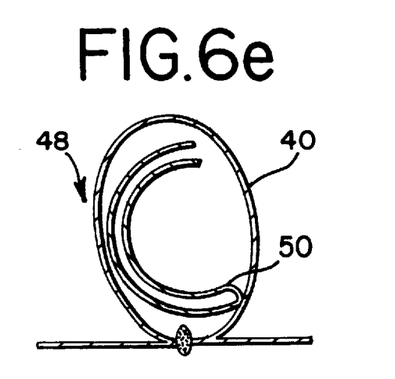

Another embodiment of the present invention is shown in FIGS. 4 and 5. In these Figures like reference numerals are used for like elements. The peaks 48 in the figures have a less rounded, more trapezoidal cross-section. In addition, the bottom portion of the peaks 48 are not encased by the facing layer 40 but by a separate piece of material denoted as a support layer 49. The facing layer 40 extends over the sides and tops of the liquid absorbent material 50 and between the individual peaks 48 while the support layer 49 extends across the bottom of the peaks 48 and bridges the spacing or channels 51 between the peaks 48, thereby securing the peaks 48 and the liner 12 as a whole.

The support layer 49 may be made from the same material as the facing layer 40 or another type of material if so desired. By using another type of material, additional fluid handling properties can be imparted to the overall structure. Here again, bonding of the support layer 49 to the facing layer 40 and the liner 12 to the overall diaper 10 can be accomplished by such means as adhesives, needling, stitching, thermomechanical and ultrasonic bonding. Additionally, the support layer 49 can contain perforations, holes, openings or voids that may align with those in the facing layer or the bottom of the peaks to facilitate fluid transfer to the absorbent core 24 disposed below the liner 12 and separation sheet 14. Basis weights for the support layer 49 in personal care applications will range between about 0.3 and about 2.5 ounces per square yard (about 10 to about 85 gsm).

Figure 7:
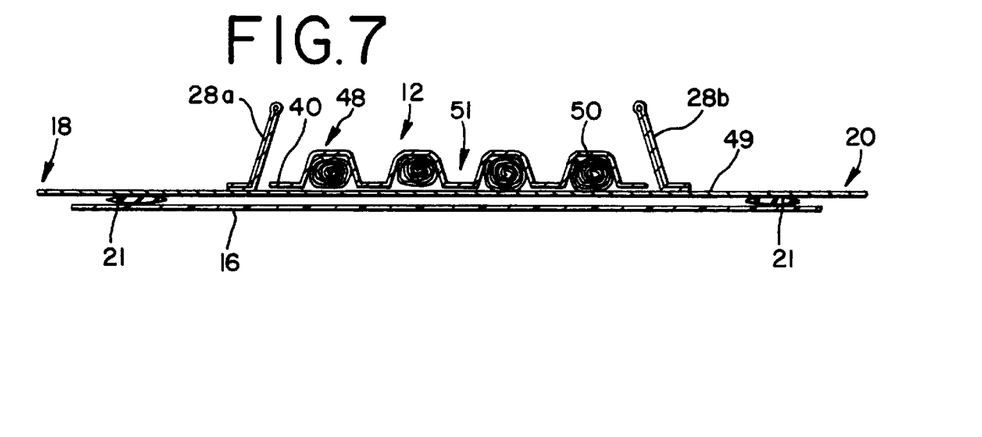
FIG. 7 is a cross-sectional side view of another diaper made in accordance with the teachings of the present invention.

Another embodiment of the present invention is shown in FIG. 7 of the drawings with like reference numerals depicting like elements. In this particular configuration, the diaper 10 has a liner 12 and a backsheet 16 but no absorbent core 24 in contrast to the embodiments shown in FIGS. 1 through 5. Consequently, the liner 12 provides a dual function in that it acts as both the liner material and the absorbent core for storing body exudates. The liner 12 can take the form of any of the embodiments described above. For example, the support layer 49 of the liner 12 can extend all the way across the backsheet 16 and be attached to the left side edge 18 and right side edge 20 or it can be attached to a separation sheet 14 in between a pair of leg dams 28a and 28b such as is shown in FIGS. 1 and 2. With this type of configuration, it may be desirable to add extra capacity to the peaks 48 as they will be the primary storage source for the body exudates.

The embodiment shown in FIG. 7 has another advantage too, especially when the backsheet 16 is made from a breathable material such as a breathable film. Because there is no absorbent core 24, the liner 12 can be in direct or near direct contact with the breathable backsheet 16. With an absorbent core 24, the backsheet 16 would only serve to pass moisture emanating from the core itself. As a result, the breathable backsheet would do very little with respect to lowering the humidity adjacent the baby's skin. Without the absorbent core, the humidified air adjacent the baby's skin has two methods to escape, out the ends of the diaper via the channels 51 and through the liner 12 again via the channels 51 and then directly through the breathable backsheet 16.

Figure 8:
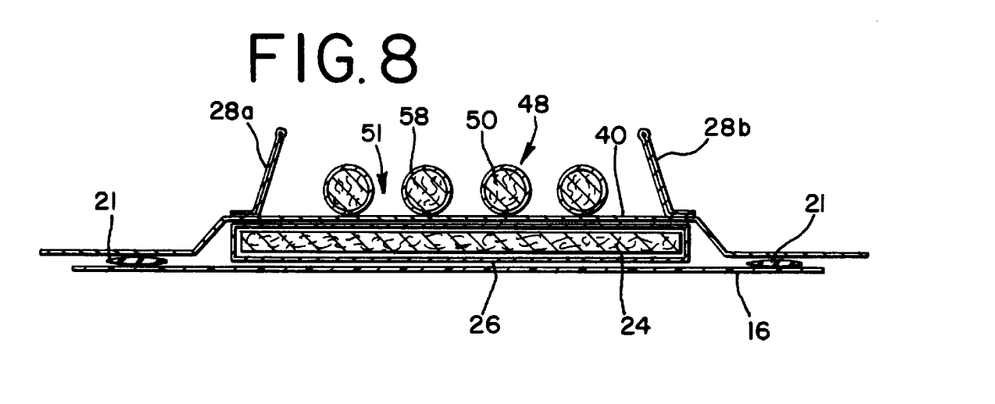
FIG. 8 is a cross-sectional side view of a diaper like that shown in FIG. 1 with an alternate embodiment of a liquid absorbing liner material according to the present invention.
Figure 9:
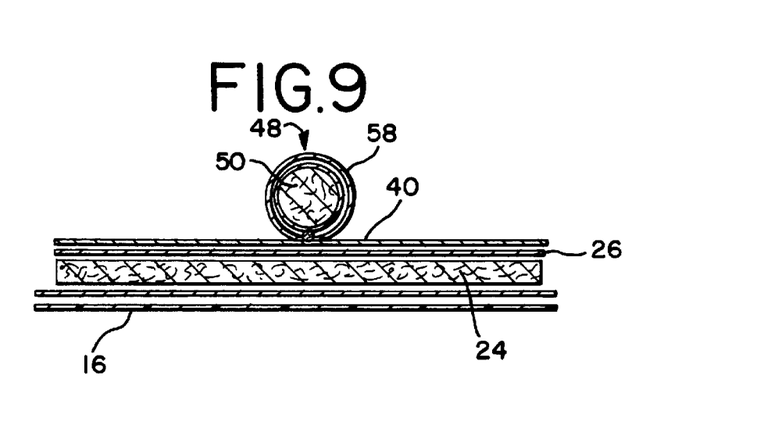
FIG. 9 is an enlarged view of one of the liquid absorbing peaks according to the present invention from FIG. 8.

Another embodiment is shown in FIGS. 8 and 9 of the drawings. In this embodiment the peaks 48 are preconstructed absorbent strips which are then attached to the exterior surface of the facing layer 40 using an adhesive or other suitable bonding means. In so doing, the peaks 48 can be custom-tailored and then unwound, for example, from a roll and then glued in place. In addition, because the peaks 48 are not formed directly into the facing layer 40, it is easier to apply the peaks 48 to the facing layer 40 in a non-linear form as, for example, in a curved pattern to match the general hour glass design of many diapers. The peaks 48, themselves, can be a single piece of material such as a foam or multiple pieces of material. Alternatively, the peaks 48 can have an outer sheath 58 akin to the facing layer 40 and an inner liquid absorbent material 50 in the same fashion as was described with the previous embodiments including the same materials and combinations.

Another embodiment (not shown) encompassed by the present invention would be the formation of openings through the liner 12 and separation sheet 14 to form a pocket into which excess urine and feces could be deposited away from the wearer of the absorbent article and closer to the absorbent core 24. These openings could also be aligned with areas of the absorbent article where a breathable backsheet was disposed directly underneath the liner 12 and separation sheet 14 to allow direct communication of the ambient air with the interior of the diaper.

Figure 10:
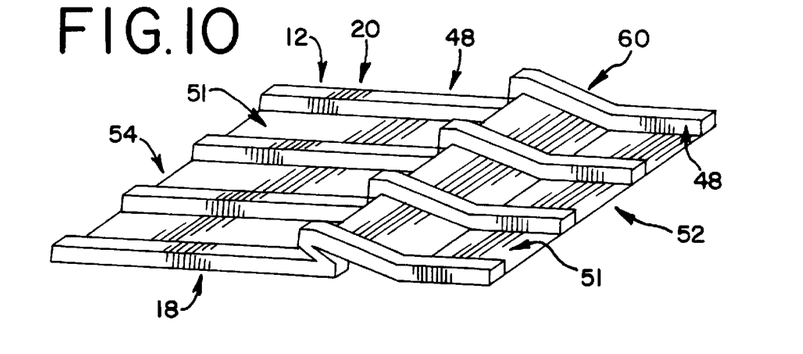
FIG. 10 is a perspective view of a liquid absorbing liner material according to the present invention with a dam formed across the material to impede liquid flow along the channels in between the peaks.

Another embodiment of a liquid absorbing liner material is shown in FIG. 10 of the drawings. FIG. 10, shows the liner material 12 only, without the remainder of the diaper components such as the absorbent core 24 and backsheet 16. The unique feature of FIG. 10 is the dam 60. The liner 12, has a left side edge 18, a right side edge 20, a top back edge 52 and a top front edge 54. The dam 60 is formed by a "Z" fold in the liner 12 which extends across the liner 12 in a direction generally parallel to at least one of the top front edge 54 and the top back edge 52. As body exudates such as urine and feces flow along the channels 51 toward the top back edge 52, the "Z" fold, formed by two parallel fold lines, creates a dam 60 to block flow or at least impede the flow of the body exudates out the end of the diaper. This is possible without significantly disturbing air flow because the peaks 48, having been folded back on themselves, still provide the channels 51 for air flow.

Figure 11:
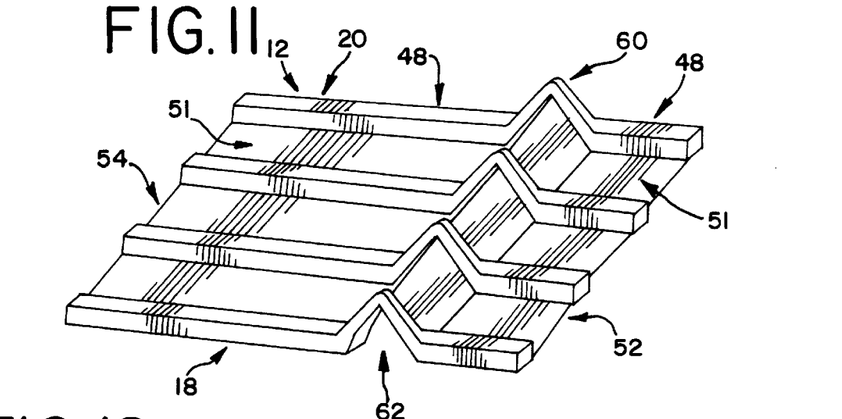
FIG. 11 is a perspective view of a liquid absorbing liner material according to the present invention with another dam formed across the material to impede liquid flow along the channels in between the peaks.

In a similar fashion, another liner 12 with a dam 60 is shown in FIG. 11 of the drawings. In this configuration, the dam 60 again extends across the width of the liner 12 in a direction generally parallel to at least one of the top front edge 54 and the top back edge 52. The dam 60 in FIG. 11 is formed from a series of three folds which forms an inverted "U" or "V" shape. If desired, the area 62 below the dam 60 can be filled with additional absorbent core material (not shown) to maintain the upright posture of the dam 60 during use.

Figure 12:
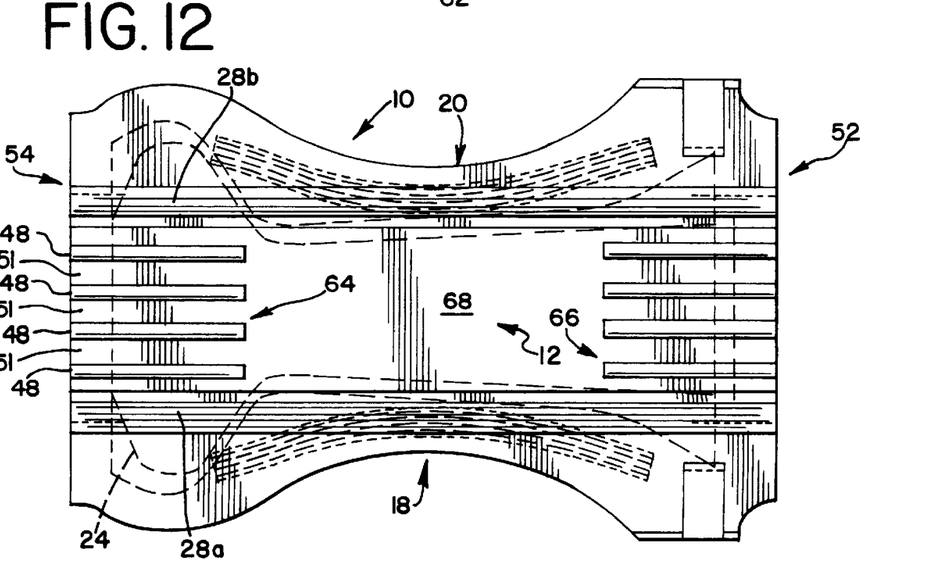
FIG. 12 is a top plan view of a personal care absorbent article, in this case a diaper, utilizing a liquid absorbing liner material according to the present invention.

Yet another embodiment of the present invention is shown in FIG. 12 of the drawings. In this embodiment, the liner 12 defines a front portion 64 adjacent the top front edge 54, and a back portion 66 adjacent the top back edge 52 with the front portion 64 and back portion 66 being separated by a central portion 68. As can be seen from FIG. 12, the front and back portions 64 and 66 have a plurality of peaks 48 and channels 51 which extend inwardly into the diaper 10 from the top front and back edges 54 and 52. The peaks 48 and channels 51 extend sufficiently into the diaper 10 to overlap the absorbent core 24 but the central portion 68 of the liner 12 is essentially devoid of any peaks 48 and channels 51. Thus the central portion 68 is more like a normal diaper design but the front and back portions 64 and 66 of the diaper 10 are still provided with the peaks 48 and channels 51 so as to permit air flow and dehumidification of the diaper 10.

With any of the foregoing embodiments the degree of humidity within the overall diaper design can be further reduced by making the backsheet 16 vapor permeable. Typically, diapers backsheets are made from polyethylene films or other polymer formulations. It is also possible to make the backsheet from materials which are breathable such as microporous meltblown nonwoven webs and porous films such as plastic films which have fillers including calcium carbonate and which are subsequently stretched or crushed to make them breathable. The more breathable the backsheet is, the better able the diaper will be to reduce the humidity. In addition, it is possible to make film/nonwoven laminates to improve the comfort and feel of the backsheet.

Having thus described the invention, several examples of the invention were prepared and are set forth below. A diaper was used as the tested construction but this should not be construed as a limitation as to the scope of use of the present invention.

EXAMPLES

In Examples 1 through 6, a series of liquid absorbing liner materials were prepared according to the present invention. The examples outlined below demonstrate a wide variety of material constructions and combinations which can be used in a variety of situations not the least of which is as a liner material for personal care absorbent articles. In Example 6, a series of diaper constructions were prepared.

Example 1

In Example 1 a liner material was made in a fashion similar to that shown in FIG. 4 and included seven peaks with two different liquid absorbent material constructions. The three center peaks had the same construction. The four outboard peaks, two on either side of the three inboard peaks had a second and different construction. The liner material was 4 inches (10 centimeters) wide and the peaks were equally spaced. Peak diameters were ½ inch (12.7 millimeters).

The facing layer was a two layer structure having a total basis weight of 1.5 ounces per square yard (50.9 grams per square meter) with the outermost layer having a basis weight of 0.5 ounces per square yard (17.0 grams per square meter) and the innermost layer, which was adjacent the liquid absorbing material, having a basis weight of 1.0 ounce per square yard (33.9 grams per square meter). The outermost layer was a through air-bonded carded web constructed entirely from three denier, 1.5 inch (38 millimeters) long bicomponent staple fibers made of polyethylene sheaths and polyester cores from the BASF Corporation, Fibers Division located in Enka, N.C. The innermost layer adjacent the liquid absorbing material was a blend of both regular and bicomponent staple fibers. The blend included 60%, based upon the total weight of fibers, 6 denier by 2 inch (51 millimeters) long polyester staple fibers from Hoechst-Celanese Corporation, Textile Fibers Group of Charlotte, North Carolina; 35% 1.5 denier by 1.5 inch (38 millimeters) long Chisso ES polyethylene sheath/polypropylene core bicomponent fibers and 5% 2 denier by 1.5 inch (38 millimeters) long Chisso ES-HB polyethylene sheath/polypropylene core bicomponent fibers from Chisso Corporation of Osaka, Japan. The blend of three fibers was thoroughly mixed and then converted into a through air-bonded carded web. Both layers of the facing layer were in turn heat bonded to one another to form a composite facing material. The fibers in both layers had been treated with a surfactant by the fiber manufacturer to make them hydrophilic.

The support layer was a 2.2 ounce per square yard (75 gram per square meter) hydroentangled pulp sheet made with Kimberly-Clark Longlac 19 soft wood pulp fibers which was treated with 1% by weight of the pulp sheet, AROSURF® PA727 surfactant from Witco Chemical Corporation, Organics Division located in Melrose, Ill.

The three center peaks were filled with 1.5 inch (38 millimeters) wide strips of the same material used to make the facing layer. The length of the strips was commensurate with the lengths of the peaks. The strips of material were folded in a general "U" shape with the outermost layer on the outside and placed within the three center peaks. The four outboard peaks, two on either side of the three center peaks, were filled with composite materials made from 1 inch (25.4 millimeters) wide strips of tissue wrapped around a superabsorbent/wood pulp fluff composite. The composite was a 50/50 weight percent basis blend of Kimberly-Clark CR54 wood pulp fluff and Sanwet® IM-3900 superabsorbent particles from Hoechst-Celanese located in Portsmouth, Va. The superabsorbent/wood pulp fluff composite had a basis weight of 11.3 ounces per square yard (384 gsm). The superabsorbent/wood pulp fluff composite was wrapped with the 1 inch (25.4 mm) wide strips of tissue wrap having a basis weight of 1.1 ounces per square yard (38.75 gsm) and the wrapped composite was placed within the four outboard peaks. The backing layer was then attached to the facing layer using an aerosol can spray adhesive designated Super 77 adhesive from 3M Industrial Specialties, a division of 3M located in St. Paul, Minn.

The resultant liner material demonstrated an embodiment wherein the facing layer was a two layer structure with a backing layer which was different than the facing layer. The three center peaks were designed with the function of temporary fluid handling while the outboard peaks containing the superabsorbent performed the function of fluid retention. When such a design is used in, for example, a diaper, the three center peaks will act to quickly absorb and temporarily store an insult of urine. Once the insult is complete, the liquid from the three center peaks will be transferred/desorbed via the backing layer into the absorbent core of the diaper and/or the outboard peaks which have their own liquid retention capability. The outboard peaks, which contain superabsorbent, will act as fluid reservoirs thereby adding extra capacity to the diaper and providing a possible barrier to leakage of urine out the sides of the diaper.

Example 2

In Example 2 a 3.5 inch (8.9 centimeters) wide liquid absorbing liner material having six peaks was prepared. The six peaks were ½ inch (12.7 millimeters) in diameter and equally spaced from one another. The six peaks had three separate compositions with the two central peaks having one composition. The peaks on either side of the two center peaks had a different composition and the two exterior or outboard peaks had yet another composition. Again each of the peaks included a facing layer, a liquid absorbent material and a backing layer. The facing layer and the backing layer were the same materials described in Example 1. The center two peaks were filled with additional facing layer material, in this case, 1 inch (2.54 cm) wide pieces of the facing layer with lengths commensurate with the overall lengths of the samples. The peaks adjacent the center peaks were filled with ¾ inch (19 mm) wide strips of the superabsorbent/fluff composite material of the same construction described in Example 1 while the outermost peaks were filled with wider, 1 inch (2.54 cm) wide strips of the same superabsorbent/fluff composite material as described in Example 1. The hydroentangled backing layer was again attached to the facing layer material using the same adhesive as in Example 1 to create a structure similar to that shown in FIG. 4 of the drawings. With the construction of Example 2, a liquid absorbing liner material was created which had center peaks which would rapidly take-up any deposited liquid while the outer peaks had increasingly higher liquid retention capabilities. When used in conjunction with a diaper, the material of Example 2 would have the ability to rapidly take in an insult of a body liquid such as urine. The two center peaks would act as a temporary reservoir for the deposited liquid. As the liquid drained out of the two center peaks, it could either pass into and through the backing layer and thus into the absorbent core below and/or migrate to the outboard peaks for additional retention and storage. In addition, if the insult of urine was particularly great, the outermost peaks due to their superabsorbent/fluff composite would act to aid in the prevention of any side leakage out the leg openings of the diaper which is often a problem.

Example 3

In Example 3, another six peak liquid absorbing liner material was created with peaks having varying dimensions. The overall structure had a width of 3-½ inches (89 mm) with the diameter of the peaks gradually increasing from the middle of the liner material to the sides. Again, spacing between the peaks was in the range of half an inch (12.7 mm) with spacing between the peaks being relatively equal. The facing layer in Example 3 was a single layer construction made from a 0.6 ounce per square yard (20.3 gsm) thermally bonded carded web material utilizing 100% three denier bicomponent staple fibers from the BASF Corporation of Enka, N.C. The fibers were 1.5 inches (38 mm) in length and had a polyethylene sheath surrounding a polyester core. The backing layer was also a single layer structure, in this case, a 0.6 ounce per square yard (20.3 gsm) through-air bonded carded web made completely from 1.8 denier polyethylene sheath/polypropylene core bicomponent fibers having a length of 1.5 inches (38 mm) from the BASF Corporation. The two innermost peaks had diameters of 5/16 of an inch (8 mm) while the peaks on either side of the inner peaks had diameters of ½ inch (12.7 mm) and the outboard peaks had diameters of ¾ inch (19 mm).

The material for the two center peaks was a 1.5 ounce per square yard (51 gsm) spunbonded material using 3 denier polyethylene/polypropylene side-by-side bicomponent fibers treated with 0.4 weight percent, based upon the total weight of the web, with Y-12488 surfactant available from OSI Specialties, Inc. of Danbury, Conn. The surf actant was a polyalkylene oxide modified polydimethyl siloxane. The polyethylene and polypropylene used to make the fibers included blue pigment so that when the material was added to the two center peaks, a visual distinctiveness was imparted. Two inch wide (51 mm) strips of the bicomponent spunbond material were cut, folded and placed inside the two center peaks.

The single peaks on either side of the two center peaks contained 1.5 inch wide (38 mm) strips of the same material used for the center peaks wrapped around 1 inch wide (25.4 mm) strips of the same hydroentangled wood pulp sheets described in Example 1. The wood pulp sheets in turn were filled with 0.15 grams of Abscents® 5000 odor control particles per 20 inches (51 cm) of length. Abscents® 5000 particles are available from UOP of Tarrytown, N.Y.

The two outermost peaks were filled with 1 inch wide strips of the previously described 2.2 ounce per square yard (75 gsm) hydroentangled Longlac 19 pulp webs treated with 1 percent AROSURF® PA727 surfactant wrapped around 1.5 inch (38 mm) wide strips of the 11.3 ounces per square yard (384 gsm) superabsorbent particle/wood pulp fluff air laid composite described in Example 1. Once all six of the peaks had been filled, the backing layer was adhesively attached to the facing layer to create a structure similar to that shown in FIG. 4 of the drawings.

This particular sample resulted in a liquid absorbing liner material made from multiple materials including natural fluff fiber webs, staple fiber webs and spunbond webs. The sample also had varying peak heights or diameters and individual peaks with varying properties and capacities. For example, the center peaks were designed to rapidly take in fluids while the peaks adjacent the center peaks were designed to take-up fluid, transfer and/or retain the fluid and lastly, reduce odor due to the odor reducing particles. As with the other two examples, the outermost peaks would have high liquid retention capability due to the use of superabsorbent particles.

Example 4

In Example 4, a 3.75 inch (95 mm) wide sample was prepared with four inner peaks having diameters of 5/16 of an inch (8 mm) and two outer peaks, one on either side of the four inner peaks having ½ inch (12.7 mm) diameters. Spacing between the peaks was uniform. The facing layer and the backing layer for Example 4 were made from the same materials described with respect to Example 3. The four inner peaks were filled with 1 inch (25.4 mm) wide strips of the blue bicomponent spunbond material from Example 3 wrapped around 0.25 inch (6 mm) wide cores of the superabsorbent/fluff composite described in Example 1. The two outboard peaks also used ½ inch (12.7 mm) wide pieces of the superabsorbent/fluff composite wrapped within 1 inch (25.4 mm) wide strips of the previously described 2.2 osy (75 gsm) hydroentangled Longlac 19 pulp webs. Once the six peaks were filled, the backing layer was secured to the facing layer using adhesive to form a liquid absorbing liner material similar in design to that shown in FIG. 4 of the drawings.

Example 4 demonstrated that the four inner peaks could be made from the same material and the two outboard peaks could be made from a different material. In addition, this example demonstrated that the peaks could contain multiple materials with multiple functionalities such as temporary fluid handling capacity in the four central peaks and fluid retention in the two outboard peaks. In addition, the two outboard peaks used multiple wood pulp fiber types in their construction.

Example 5

In Example 5, a series of fifteen samples were prepared. Each of these samples used the same facing layer and backing layer as described in Example 4 with the variable being the material or materials used to fill the peaks. Each of the samples contained four ⅜ inch (9.5 mm) high by one-half inch (12.7 mm) wide peaks spaced ⅜ of an inch (9.5 mm) apart over the width of the 4 inch (10 cm) sample. The liquid absorbent materials used to fill all fifteen of the samples were made from bonded carded webs having varying fiber compositions. See Table I below. All basis weights for the liquid absorbing materials were 2.5 ounces per square yard (85 gsm) except as noted with respect to samples A, B and O. The percentage of fibers indicated in Table I are given on a weight percent basis, based upon the total weight of the particular web or layer in question. As with the other examples, once the peaks were filled, the backing layer was adhesively attached to the liner material to create liquid absorbent liner materials similar in construction to that shown in FIG. 2 of the drawings. The filler material for sample O was a needled batt of 5.5 denier Courtaulds 20762 rayon fibers printed bonded with 2.5% (based upon the total weight of the fabric) latex that was pigmented 0.2% (based upon the total weight of the fabric) blue pigment. The fabric is available as SN-92 from Sackner Products of Grand Rapids, Mich. and the fibers making the web were from Courtaulds Fibers, Inc. of Axis, Ala. This example demonstrated an extremely crush resistant material that while providing the desired humidity and skin hydration reduction, would not handle fluid as well as Example 5C. Example 5C had a more desirable open structure to absorb and release large volume insults that occur in many absorbent articles.

TABLE I

| SAMPLE | BASIS WT. (osy/gsm) | CORE FIBER COMPOSITION (weight percent) |
|---|---|---|
| A | 2.65/90 | 60% 3.0d PE/PET[1] |
|  |  | 35% 1.8d PE/PET[2] |
|  |  | 5% 2.0d PE/PP[3] |
| B | 3.5/120 | 60% 3.0d PE/PET[1] |
|  |  | 35% 1.8d PE/PET[2] |
|  |  | 5% 2.0d PE/PP[3] |
| C | 2.5/85 | 70% 6.0d PE/PET[4] |
|  |  | 15% 6.0d rayon[5] |
|  |  | 15% 6.0d PET[6] |
| D | 2.5/85 (total) |  |
|  | 1.5/51 | Layer 1 |
|  |  | 60% 3.0d PE/PET[1] |
|  |  | 20% 6.0d rayon[5] |
|  |  | 20% 6.0d PET[6] |
|  | 1.0/34 | Layer 2 |
|  |  | 40% 3.0d PE/PET[1] |
|  |  | 60% 6.0d rayon[4] |
| E | 2.5/85 | 60% 3.0d PE/PET[1] |
|  |  | 40% 6.0d PET[6] |

TABLE I-continued

| SAMPLE | BASIS WT. (osy/gsm) | CORE FIBER COMPOSITION (weight percent) |
|---|---|---|
| F | 2.5/85 | 60% 3.0d PE/PET[1] |
|   |   | 40% 6.0d rayon[5] |
| G | 2.5/85 | 50% 1.8d PE/PET[2] |
|   |   | 50% 3.0d PE/PET[1] |
| H | 2.5/85 | 100% 6.0d PE/PET[5] |
| I | 2.5/85 | 40% 1.8d PE/PET[2] |
|   |   | 30% 1.5d rayon[7] |
|   |   | 30% 6.0d PET[6] |
| J | 2.5/85 | 60% 3.0d PE/PET[1] |
|   |   | 20% 6.0d rayon[5] |
|   |   | 20% 6.0d PET[6] |
| K | 2.5/85 | 70% 3.0d PE/PET[1] |
|   |   | 20% 6.0d rayon[5] |
|   |   | 10% 6.0d PET[6] |
| L | 2.5/85 | 80% 3.0d PE/PET[1] |
|   |   | 20% 6.0d PET[6] |
| M | 2.5/85 | 80% 3.0d PE/PET[1] |
|   |   | 20% 6.0d rayon[5] |
| N | 2.5/85 (total) |   |
|   | 1.5/51 | Layer 1 |
|   |   | 40% 1.8d PE/PET[2] |
|   |   | 30% 1.5d rayon[7] |
|   |   | 30% 6.0d PET[6] |
|   | 1.0/34 | Layer 2 |
|   |   | 40% 1.8d PE/PET[2] |
|   |   | 60% 1.5d rayon[7] |
| O | 3.5/120 | 100% 5.5d rayon[8] |

[1]BASF Corp. CS-2 fiber
[2]BASF Corp. CS-1 fiber
[3]Chisso Corp. ES-HB fiber
[4]BASF Corp. CS-1 fiber
[5]Courtaulds Fibers, Inc. lot 1685 fiber
[6]Hoeschst Celanese Corp. Type 295 fiber
[7]Courtaulds Fibers Inc lot 1089 fibers
[8]Produced by Sackner Products at Grand Rapids, Michigan Example 5 demonstrated that the liquid absorbing material or filler for the peaks can be made from a wide variety of materials including both bicomponent and plain staple fiber constructions. As with the other examples, specific functionality can be built into the particular peaks by selectively choosing appropriate fibers and other components which, when combined, will meet a particular need.

Example 6

In Example 6, sample diapers were prepared using the liner composites from samples 5C and 5F from Example 5. The liner materials were glued to the separation layer of a diaper construction similar to that shown in FIGS. 1, 5 and 6 using a hot melt adhesive 34-5563 from the National Starch Company of Bridgewater, N.J. Attached to the separation layer on either side of the liner material and inboard from the side edges of the diaper were a pair of leg dams. The separation layer was made from a 0.6 osy (20 gsm) thermally bonded polypropylene spunbond web which was treated with 0.4%, based on the weight of the fabric, Triton® X-102 surfactant from Union Carbide Corp. of Sistersville, W. Va.

The absorbent core used for sample 6A and sample 6B was comprised of an approximate 50%/50% blend of superabsorbent material (Hoechst-Celanese IM-3900 superabsorbent particles) and wood pulp fluff with a density range of 0.22–0.24 grams per cubic centimeter. The absorbent core was encased between two layers of tissue which functioned to contain the absorbent core which in turn prevented the superabsorbent and fluff material from migrating toward the wearer of the undergarment or toward the backsheet. One of the tissues was a high porosity, low basis weight tissue used in processing the absorbent core. The top (toward wearer) tissue was a high-basis weight, low porosity tissue that functioned as a barrier sheet to prevent the absorbent core materials from exiting the absorbent core composite.

For sample 6A, the liner material was the same as that described in Example 5C and ran the entire length of the diaper from the front waistband to the back waistband between the leg dams and was joined to the separation layer with hot melt adhesives. The backsheet was made from a 1.32 mil (33.5 microns) thick N-TAF-CT Espoir® breathable microporous film available from Consolidated Thermoplastics Co. of Schaumburg, Ill. For Example 6B, the liner material was the same as that described in Example 5F and also ran the entire length of the diaper from the front waistband to the back waistband between the leg dams and was joined to the separation layer with hot melt adhesives. The backsheet was a laminate of a stretch thinned 0.35 mil (8.9 microns) thick breathable calcium carbonate loaded polyethylene-based microporous film thermally bonded to a 0.5 osy (17 gsm) 1.5 denier per fiber polypropylene spunbonded nonwoven web. With all samples, the separation layers were joined about their edges to the backsheets with National Starch 34-5563 hot melt adhesive with waist and leg elastics disposed between the separation layers and the backsheet.

All samples of the diapers were insulted with saline solution and then evaluated for skin hydration effects and humidity reduction. All the diapers showed reductions in skin hydration and humidity when compared with conventional diapers. As between samples 6A and 6B, sample 6A was better at reducing skin hydration and humidity than sample 6B.

For each of the foregoing examples, the primary purpose of the peaks was to absorb and distribute liquids to other areas of the liner material and/or the absorbent core below in the case of personal care absorbent articles. In such enduse applications the channels serve as air passages for moving and exchanging the humidified air adjacent the skin of the wearer with ambient air to reduce skin hydration. In the case of diapers, the channels also serve the function of acting as a storage place for the solids portion of any exuded feces. At the same time, the peaks act to separate the skin from at least a portion of the feces residing within the channels. Consequently, the wearer should feel more comfortable.

Having thus described the invention in detail, it should be understood that various modifications and changes can be made in the present invention without departing from the spirit and scope of the following claims.

We claim:

1. A liquid absorbing liner material comprising:
   a facing layer and a support layer, said facing layer and said support layer being liquid permeable, said facing layer being joined to said support layer by a plurality of spaced-apart bonds, said facing layer and support layer within pairs of said bonds forming peaks, said peaks being spaced from one another by channels, and
   a liquid absorbing material disposed within said peaks for receiving liquids.

2. A personal care absorbent article comprising:
   a liner material and a backsheet with an absorbent core disposed therebetween said liner material comprising a facing layer and a support layer, said facing layer being joined to said support layer by a plurality of spacedapart bonds, said facing layer and support layer within pairs of said bonds forming peaks, said peaks being spaced from one another by channels, and a liquid absorbing material disposed within said peaks for receiving body exudates.

3. The personal care absorbent article of claim 2 wherein at least one of said peaks further contains a superabsorbent material.

4. The personal care absorbent article of claim 2 wherein at least one of said peaks further contains an odor reducing agent.

5. The personal care absorbent article of claim 2 wherein said facing layer is made from a fibrous nonwoven web.

6. The personal care absorbent article of claim 5 wherein said fibrous nonwoven web includes bicomponent fibers.

7. The personal care absorbent article of claim 5 wherein said liquid absorbing material disposed within said peaks is a fibrous nonwoven web.

8. The personal care absorbent article of claim 7 wherein said fibrous nonwoven web contained within said peaks has opposing first and second exterior surfaces and a plurality of pores dispersed within said web, said web defining a pore size gradient from said first exterior surface to said second exterior surface, said pores adjacent said first exterior surface being larger than said pores adjacent said second exterior surface.

9. The personal care absorbent article of claim 8 wherein said fibrous nonwoven web within said peaks is folded over on itself such that said second exterior surface contacts itself.

10. The personal care absorbent article of claim 7 wherein said fibrous nonwoven web contained within said peaks is made from a blend including polyethylene sheath/polyester core bicomponent fibers, rayon fibers and polyester fibers.

11. The personal care absorbent article of claim 2 wherein said liquid absorbing material contacts said support layer.

12. The personal care absorbent article of claim 2 wherein said liner material is separated from said absorbent core by a separation layer of fibrous nonwoven web material.

13. The personal care absorbent article of claim 12 wherein said separation layer is joined to said backsheet along a left side edge and a right side edge with said absorbent core disposed between said backsheet and said separation layer.

14. The personal care absorbent article of claim 13 wherein said liner material is attached to said separation layer on a side of said separation layer opposed from said absorbent core, said separation layer further including leg dams extending upwardly from a same side of said separation layer as said liner material, said leg dams and said left and right side edges defining zones between said leg dams and said left and right sides respectively which are essentially devoid of said liner material.

15. The personal care absorbent article of claim 14 wherein said backsheet is breathable.

16. The personal care article of claim 2 wherein said article defines a front edge, a back edge, a left side edge and a right side edge, said liner material further defining a front portion adjacent said front edge and a back portion adjacent said back edge, said front portion and said back portion being separated by a central portion, said central portion being devoid of said peaks.

17. A liquid absorbent liner material comprising:

a facing layer containing a plurality of pairs of first and second folds, each of said first and second folds forming respective first and second fold lines, said facing layer being joined to itself generally along said first and second fold lines to form a plurality of spaced-apart peaks, said peaks being spaced from one another by channels, and a liquid absorbing material disposed within said peaks for receiving liquids.

18. A personal care absorbent article comprising:

a liner material and a backsheet with an absorbent core disposed therebetween, said liner material comprising a facing layer containing a plurality of pairs of first and second folds, each of said first and second folds forming respective first and second fold lines, said facing layer being joined to itself generally along said first and second fold lines to form a plurality of spaced-apart peaks, said peaks being spaced from one another by channels, and a liquid absorbing material disposed within said peaks for receiving body exudates.

19. The personal care absorbent article of claim 18 wherein at least one of said peaks further contains a superabsorbent material.

20. The personal care absorbent article of claim 18 wherein at least one of said peaks further contains an odor reducing agent.

21. The personal care absorbent article of claim 18 wherein said facing layer is made from a fibrous nonwoven web.

22. The personal care absorbent article of claim 21 wherein said fibrous nonwoven web includes bicomponent fibers.

23. The personal care absorbent article of claim 21 wherein said liquid absorbing material disposed within said peaks is a fibrous nonwoven web.

24. The personal care absorbent article of claim 23 wherein said fibrous nonwoven web contained within said peaks has opposing first and second exterior surfaces and a plurality of pores dispersed within said web, said web defining a pore size gradient from said first exterior surface to said second exterior surface, said pores adjacent said first exterior surface being larger than said pores adjacent said second exterior surface.

25. The personal care absorbent article of claim 24 wherein said fibrous nonwoven web within said peaks is folded over on itself such that said second exterior surface contacts itself.

26. The personal care absorbent article of claim 18 wherein said liner material is separated from said absorbent core by a separation layer of fibrous nonwoven web material.

27. The personal care absorbent article of claim 26 wherein said separation layer is joined to said backsheet along a left side edge and a right side edge with said absorbent core disposed between said backsheet and said separation layer.

28. The personal care absorbent article of claim 27 wherein said liner material is attached to said separation layer on a side of said separation layer opposed from said absorbent core, said separation layer further including leg dams extending upwardly from a same side of said separation layer as said liner material, said leg dams and said left and right side edges defining zones between said leg dams and said left and right sides respectively which are essentially devoid of said liner material.

29. The personal care absorbent article of claim 28 wherein said backsheet is breathable.

30. A personal care absorbent article comprising:

a liner material and a backsheet joined to said liner material, said liner material comprising a facing layer and a support layer, said facing layer being joined to said support layer by a plurality of spaced-apart bonds, said facing layer and support layer within pairs of said bonds forming peaks, said peaks being spaced from one another by channels, and a liquid absorbing material disposed within said peaks for receiving body exudates.

31. The personal care absorbent article of claim 30 wherein said backsheet is breathable.

32. The personal care absorbent article of claim 31 wherein said liner material forming said channels is in contact with said breathable backsheet.

33. The personal care absorbent article of claim 30 wherein said article defines a front edge, a back edge, a left side edge and a right side edge, said liner material having a dam extending across said liner material in a direction generally parallel to at least one of said front edge and said back edge.

34. The personal care article of claim 33 wherein said dam is formed by a fold in said liner material.

35. The personal care absorbent article of claim 30 wherein said facing layer further defines a plurality of apertures extending through said facing layer.

36. The personal care absorbent article of claim 30 wherein said article defines a front edge and a back edge, a left side edge and a right side edge, said peaks having closed ends adjacent said front edge and said back edge.

37. A personal care absorbent article comprising:
a liner material and a backsheet joined to said liner material, said liner material comprising a facing layer containing a plurality of pairs of first and second folds, each of said first and second folds forming respective first and second fold lines, said facing layer being joined to itself generally along said first and second fold lines to form a plurality of spaced-apart peaks separated by channels, and
a liquid absorbing material disposed within said peaks for receiving body exudates.

38. The personal care absorbent article of claim 37 wherein said backsheet is breathable.

39. A personal care absorbent article comprising:
a liner material and a backsheet with an absorbent core disposed therebetween, said liner material comprising a facing layer with a plurality of liquid absorbent peaks attached at spaced-apart intervals to a surface of said facing layer opposed to said backsheet and absorbent core.

40. A personal care absorbent article comprising:
a liner material and a backsheet joined to said liner material, said liner material comprising a facing layer with a plurality of liquid absorbent peaks attached at spacedapart intervals to a surface of said facing layer opposed to said backsheet.

41. The personal care absorbent article of claim 40 wherein said backsheet is breathable.

42. A personal care absorbent article comprising a liner material and a backsheet,
said liner material comprising a plurality of peaks on its surface opposed to said backsheet at spaced-apart intervals separated by channels, said liner material being joined to said backsheet along a left side edge and a right side edge;
a liquid absorbing material disposed within said peaks for receiving body exudates; and
leg dams interior to said left and right side edges.

43. The personal care absorbent article of claim 42 wherein said channels extend to the longitudinal ends of the article and permit air flow along the length of the liner material in use.

44. The personal care absorbent article of claim 42, further comprising:
an absorbent core disposed between said liner material and backsheet, and wherein said liner material comprises a facing layer and a support layer, said facing layer being joined to said support layer by a plurality of spaced-apart bonds, said facing layer and said support layer between pairs of bonds forming said peaks.

45. The personal care absorbent article of claim 42, further comprising:
an absorbent core disposed between said liner material and backsheet, and wherein said liner material comprises a facing layer containing a plurality of pairs of first and second folds, each of said first and second folds forming respective first and second fold lines, said facing layer being joined to itself generally along said first and second fold lines to form said plurality of spaced-apart peaks.

46. The personal care absorbent article of claim 42, further comprising:
an absorbent core disposed between said liner material and backsheet and wherein said liner material comprises a facing layer with a plurality of liquid absorbent peaks attached at spaced-apart intervals to the surface of said facing layer opposed to said backsheet and absorbent core.

47. The personal care absorbent article of claim 44 wherein said liner material is separated from said absorbent core by a separation layer of fibrous nonwoven web material.

48. The personal care absorbent article of claim 47 wherein said separation layer is joined to said backsheet along a left side edge and a right side edge with said absorbent core disposed between said backsheet and said separation layer.

49. The personal care absorbent article of claim 48 wherein said liner material is attached to said separation layer on a side of said separation layer opposed from said absorbent core, said separation layer further including said leg dams extending upwardly from a same side of said separation layer as said liner material, said leg dams and said left and right side edges defining zones between said leg dams and said left and right sides respectively which are essentially devoid of said liner material.

50. The personal care absorbent article of claim 42 wherein said liner material comprises a facing layer and a support layer, said facing layer being joined to said support layer by a plurality of spaced-apart bonds, said facing layer and said support layer between pairs of bonds forming said peaks.

51. The personal care absorbent article of claim 42 wherein said liner material comprises a facing layer containing a plurality of pairs of first and second folds, each of said first and second folds forming respective first and second fold lines, said facing layer being joined to itself generally along said first and second fold lines to form said plurality of spaced-apart peaks separated by channels.

52. The personal care absorbent article of claim 42 wherein said liner material comprises a facing layer with a plurality of liquid absorbent peaks attached at spacedapart intervals to a surface of said facing layer opposed to said backsheet.

53. The personal care absorbent article of claim 42 wherein said backsheet is breathable.

54. The personal care absorbent article of claim 42 wherein at least one of said peaks further contains a superabsorbent material.

55. The personal care absorbent article of claim 42 wherein at least one of said peaks further contains an odor reducing agent.

56. The personal care absorbent article of claim 42 wherein said liquid absorbing material disposed within said peaks is a fibrous nonwoven web.

57. The personal care absorbent article of claim 56, wherein said fibrous nonwoven web contained within said peaks has opposing first and second exterior surfaces and a plurality of pores dispersed within said web, said web defining a pore size gradient from said first exterior surface to said second exterior surface, said pores adjacent said first exterior surface being larger than said pores adjacent said second exterior surface.

59. The personal care article of claim 42 wherein said article defines a front edge, a back edge, a left side edge and a right side edge, said liner material further defining a front portion adjacent said front edge and a back portion adjacent said back edge, said front portion and said back portion being separated by a central portion, said central portion being devoid of said peaks.

58. The personal care absorbent article of claim 57, wherein said fibrous nonwoven web within said peaks is folded over on itself such that said second exterior surface contacts itself.

60. The personal care absorbent article of claim 42 wherein said article defines a front edge, a back edge, a left side edge and a right said edge, said liner material having a dam extending across said liner material in a direction generally parallel to at least one of said front edge and said back edge.

* * * * *